United States Patent [19]

Goetz et al.

[11] Patent Number: 4,504,363

[45] Date of Patent: Mar. 12, 1985

[54] PREPARATION OF CIS-2,6-DIMETHYLMORPHOLINE

[75] Inventors: Norbert Goetz, Worms; Bjoern Girgensohn, Mannheim; Fritz Zanker, Worms, all of Fed. Rep. of Germany

[73] Assignee: BASF Aktiengesellschaft, Fed. Rep. of Germany

[21] Appl. No.: 491,778

Foreign Application Priority Data

May 13, 1982, [DE] Fed. of Germany .......... 3217964

[22] Filed: May 5, 1983

[51] Int. Cl.$^3$ ................................................ C07B 5/00
[52] U.S. Cl. ............................ 203/14; 203/DIG. 6; 544/106
[58] Field of Search ............ 544/106; 203/14, DIG. 6

[56] References Cited

U.S. PATENT DOCUMENTS

| | | | |
|---|---|---|---|
| 3,083,202 | 3/1963 | Summers | 260/247 |
| 4,212,972 | 7/1980 | Goetz et al. | 544/106 |
| 4,298,733 | 11/1981 | Goetz et al. | 544/106 |

FOREIGN PATENT DOCUMENTS 1086734  9/1980  Canada .

OTHER PUBLICATIONS

J. Heterocycl. Chem. 17 (1980), 369–372.

*Primary Examiner*—William Smith
*Attorney, Agent, or Firm*—Keil & Weinkauf

[57] ABSTRACT

2,6-Dimethylmorpholine containing a high proportion of the cis compound is prepared by cyclization of diisopropanolamine (1,1′-iminobispropan-2-ol) in the presence of sulfuric acid, with simultaneous addition of the components and full utilization of the heat of reaction.

4 Claims, No Drawings

PREPARATION OF CIS-2,6-DIMETHYLMORPHOLINE

It has long been known that morpholines can be prepared by elimination of water from a bishydroxyalkylamine in the presence of an acidic catalyst, eg. sulfuric acid, or by vapor-phase dehydration over an aluminum oxide catalyst (Houben-Weyl, Methoden der organischen Chemie, 4th edition, Georg Thieme Verlag, Stuttgart, 1966, volume 6/4, pages 510–520). The problems arising in connection with the isolation of sterically pure compounds in the synthesis of morpholines which possess two or more substituents on the ring and are expected to form various stereoisomeric compounds in varying amounts, depending on the reaction conditions, have been reported to a lesser extent. For example, the mechanism of cyclization of 3,3'-iminobisbutan-2-ols to 2,3,5,6-tetramethylmorpholines in sulfuric acid has been investigated (J. Heterocycl. Chem. 17 (1980), 369–372).

For many purposes, cis-2,6-dimethylmorpholine is preferable to the isomer mixture. For example, the action of crop protection agents prepared from this is due principally to the compounds obtained from the cis-isomer.

A method of concentrating the cis-isomer in a mixture of 2,6-dimethylmorpholine isomers by isomerization with excess sulfuric acid or by cyclization of diisopropanolamine with concentrated sulfuric acid at from 185° to 220° C. is described in U.S. Pat. No. 3,083,202. In this process, the high reaction temperature is a disadvantage, since it is known (H. Remy, Lehrbuch der anorg. Chemie, 13th edition, Akademische Verlagsgesellschaft Geest und Portig K. G., Leipzig, 1970, volume 1, pages 861, 921 and 922) that concentrated sulfuric acid, when heated, is converted to sulfurous acid or sulfur dioxide with liberation of oxygen, and transforms organic material to carbon. The free amine (diisopropanolamine and morpholine) is particularly unstable, but the salt is more stable. Thus, according to the stated U.S. Patent, the sulfuric acid is initially taken and the amine is added slowly, while cooling and stirring, so that the temperature of the solution does not exceed 80° C. Only when all of the amine has been added to the sulfuric acid is the solution heated to about 200° C. The process is consumptive of energy and time (first cooling is required, during which the desired reaction hardly takes place, and then heating is necessary); furthermore, in our experience, the yields stated for the reaction cannot in fact be achieved since at 190° C. and above the decomposition of the salt also interferes noticeably. Instead, a large number of by-products, some of them deeply colored, are obtained, and the yields of 2,6-dimethylmorpholine are substantially lower than in the novel process.

It is an object of the present invention to provide a very economical process for the preparation of 2,6-dimethylmorpholine in very high yield and with a very high proportion of the cis compound.

We have found that this object is achieved, and that 2,6-dimethylmorpholine

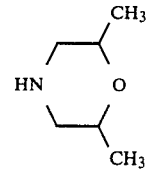

is obtained in high yield and with a high proportion of the cis compound (75–88%), if diisopropanolamine (1,1'-iminobispropan-2-ol)

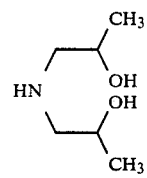

containing from 0 to 20, preferably from 5 to 15, percent by weight, based on the amine, of water and, at the same time, excess (ie. an amount such that the reaction mixture is acidic) concentrated sulfuric acid (from 90 to 120, preferably from 98 to 105, % strength), preferably in a molar ratio of amine to acid which is maintained at from 1:1.0 to 1:3.0, are introduced into a reaction vessel at a rate which is sufficiently rapid for the temperature of the mixture to increase to 85°–170° C., preferably 100°–150° C., when no cooling is employed, ie. merely natural cooling by the surrounding air in general at room temperature, the reaction is then carried out at from 150° to 190° C., preferably from 170° to 184° C. for from 1 to 25, preferably from 3 to 21, hours, any water present and/or formed being distilled off, the resulting product is stirred into dilute sodium hydroxide solution (eg. about 10–25% strength), while cooling, and the pH is thus advantageously brought to about 12–14, the organic phase formed during this procedure is distilled under reduced pressure, preferably at a bottom temperature of from 50° to 110° C., in order to separate off troublesome by-products, and the resulting distillate (crude, water-containing 2,6-dimethylmorpholine) is dried, advantageously by shaking or stirring with concentrated sodium hydroxide solution (about 50% strength) at below 40° C.

The yield is critically dependent on the fact that the two components are introduced simultaneously into the reaction space, and not in accordance with the prior art procedure, where one component (amine or sulfuric acid) is initially taken and the other added. The simultaneous addition of the components is carried out while stirring, but no particular demands are made in respect of the thoroughness with which the stirring is carried out. The component may run into the reaction vessel through the same orifice so that they are already more or less mixed before they reach the hot reaction mixture in the vessel, or they may be added through two separate orifices: the choice of the procedure is not critical.

When the novel process is employed, 98–99% pure 2,6-dimethylmorpholine is obtained, and this can be separated into pure cis-2,6-dimethylmorpholine and pure trans-2,6-dimethylmorpholine without difficulty by fractional distillation over a packed column (cf. CA 1,086,734). For total yields of 2,6-dimethylmorpholine of 90–98%, it is possible to obtain a product containing 75–88% of cis-2,6-dimethylmorpholine; an isomer ratio of about 88% of the cis compound to 12% of the trans compound corresponds to a thermodynamic equilibrium as can be established with reference to isomerization experiments over hydrogenation catalysts (cf. U.S. Pat. Nos. 4,298,733 and 4,212,972) at 170°–250° C. for long residence times. Higher proportions of the cis compound in the reaction mixture (>88%) are obtained, only at the expense of the total yield, if, in accordance with U.S. Pat. No. 3,083,202, in particular some of the thermodynamically more unstable trans-2,6-dimethylmorpholine is destroyed under very drastic reaction conditions. Thus, for example, under the reaction conditions stated in the above publication (preferred temperature from 190° to 210° C.), the oxidative properties of concentrated sulfuric acid are very noticeable, and this can be recognized from the evolution of $SO_2$ during the reaction, the formation of an amount of water substantially above the theoretical amount and the poor total yields of 2,6-dimethylmorpholine (cf. present Comparative Example). The total yields stated in the above U.S. patent could not be reproduced, in spite of very strict adherence to the reaction conditions. In the process according to the invention, the reaction is carried out at a temperature at which the oxidative action of the sulfuric acid is still insignificant. Accordingly, the advantages of the process are:

1. High total yield of 2,6-dimethylmorpholine.
2. High proportion of the cis compound.
3. Low energy consumption, because the entire heat of reaction is utilized.
4. No expense is entailed with regard to a cooling apparatus for the reaction vessel.
5. No warmed cooling water.
6. Time is saved because the reaction already begins during the addition of the components.
7. Less corrosion in the reactors as a result of the lower reaction temperature.
8. Drying the crude product with concentrated sodium hydroxide solution (from 30 to 50, preferably from 45 to 50, % strength) is particularly economical, since the dilute sodium hydroxide solution obtained in this procedure is used for neutralizing the next batch of reaction mixture.

As stated above, the two isomeric 2,6-dimethylmorpholines can be readily separated by fractional distillation (CA 1,086,734), and the undesirable trans-2,6-dimethylmorpholine can be converted to the desired product cis-2,6-dimethylmorpholine by isomerization, preferably over a hydrogenation catalyst (U.S. Pat. Nos. 4,212,972 and 4,298,733). The isomerization process described in U.S. Pat. No. 3,083,202 inevitably gives an undesirable salt load as a waste product, and is less suitable.

The diisopropanolamine used as a starting material is readily obtainable by reacting ammonia with propylene oxide (Houben-Weyl, Methoden der organischen Chemie, volume 11/1, pages 311–327).

The reaction is carried out continuously or batchwise and, apart from the sulfuric acid, in the absence of a solvent.

The cis-2,6-dimethylmorpholine prepared by the novel process is a useful intermediate for crop protection agents (CA 1,086,734 and U.S. Pat. Nos. 4,202,894 and 4,241,058).

In the Examples which follow, parts are by weight, and parts by volume bear the same relation to parts by weight as that of the liter to the kilogram.

EXAMPLE 1

(a) A mixture of 266 parts of diisopropanolamine and 30 parts of water and
(b) 255 parts of 96% strength sulfuric acid (1.25 moles of sulfuric acid per mole of diisopropanolamine)

were fed simultaneously, while stirring, into a stirred apparatus with a capacity of 1,000 parts by volume. The feed rate was set so that the temperature in the reaction space remained at from 100° to 120° C., without cooling. Thereafter, the mixture was heated to 150° C. for 21 hours, during which any water present or any water formed in the course of the reaction was distilled off continuously. The product was cooled, diluted with 200 parts of water and then fed into an initially taken amount of 800 parts of 25% strength sodium hydroxide solution, while stirring and cooling. After the addition was complete, the pH of this mixture was 14. 2 phases were formed, and the upper, organic phase was separated off and distilled under a reduced pressure of about 100 mbar to give 521 parts of distillate (a mixture of water and 2,6-dimethylmorpholine), which was dried in 2 stages, by stirring first with 300 parts by weight of 50% strength sodium hydroxide solution and then with 150 parts by weight thereof.

After this drying step, 228 parts (98% of theory) of 99% pure 2,6-dimethylmorpholine were obtained. The product contained 78% of the cis-isomer and 22% of the trans-isomer.

The dilute sodium hydroxide solution obtained in the drying step was employed for neutralizing the next batch of reaction mixture.

EXAMPLE 2

The procedure was carried out similarly to Example 1, using 1.25 moles of sulfuric acid per mole of diisopropanolamine, except that the mixture was heated at 170° C. for 12 hours. Under these conditions, 2,6-dimethylmorpholine was likewise obtained in a total yield of 98% of theory, the product containing 78% of the cis-isomer and 22% of the trans-isomer.

EXAMPLE 3

The procedure was carried out similarly to Example 1, except that 1.5 moles of sulfuric acid were employed per mole of diisopropanolamine, and the mixture was heated at 180° C. for 5 hours. Under these reaction conditions 2,6-dimethylmorpholine was obtained in a total yield of 96% of theory, the product containing 80% of the cis-isomer and 20% of the trans-isomer.

EXAMPLE 4

The procedure was carried out similarly to Example 1, except that 2.0 moles of sulfuric acid were employed per mole of diisopropanolamine, and the mixture was heated at 180° C. for 3 hours. Under these reaction conditions, 2,6-dimethylmorpholine was obtained in a total yield of 94% of theory, the product containing 84% of the cis-isomer and 16% of the trans-isomer.

EXAMPLE 5

The procedure was carried out similarly to Example 1, except that 3.0 moles of sulfuric acid were employed per mole of diisopropanolamine, and the mixture was heated at 180° C. for 3 hours. Under these conditions, 2,6-dimethylmorpholine was obtained in a total yield of 91% of theory, the product containing 88% of the cis-isomer and 12% of the trans-isomer.

EXAMPLE 6

(a) According to the Invention 245 parts of 96% strength sulfuric acid and a mixture of 266 parts of diisopropanolamine and 30 parts of water were introduced simultaneously, while stirring thoroughly, into a reactor having a capacity of 1,000 parts by volume. The temperature remained at 100–120° C., without cooling. Thereafter, the mixture was heated at 184° C. for 5 hours, during which any water present and any water formed as a result of the reaction was distilled off continuously (a total of 75 parts; theoretical amount: 76 parts of water).

The product was then run into 1,000 parts of 20% strength sodium hydroxide solution, while stirring and cooling, and the final pH of the mixture was 14. 2 phases were formed, and the upper, organic phase was separated off and distilled under a reduced pressure of about 100 mbar to give 515 parts by weight of distillate (a mixture of water and 2,6-dimethylmorpholine), which was dried in 2 stages, by stirring first with 300 parts by weight of 50% strength sodium hydroxide solution and then with 150 parts by weight thereof.

After this drying step, 216 parts by weight (93% of theory) of 99% pure 2,6-dimethylmorpholine were obtained. The product contained 78% of the cis-isomer and 22% of the trans-isomer.

(b) Comparative Experiment

The procedure was carried out similarly to Example 6a, except that the mixture of diisopropanolamine and water was initially introduced and the concentrated sulfuric acid was added to the stirred mixture at from 100° to 120° C. This procedure resulted in undesirable side reactions (cracking and resin-forming processes) with the formation of increased amounts of oily and tar-like by-products, which remained in the distillation residue when the crude 2,6-dimethylmorpholine was distilled. The total yield of 2,6-dimethylmorpholine was 78% of theory in this case, and the product likewise contained 78% of the cis-isomer and 22% of the trans-isomer.

(c) Comparative Experiment

The procedure was carried out similarly to Example 6a, except that the concentrated sulfuric acid was initially introduced and the mixture of diisopropanolamine and water was pumped in at from 100° to 120° C. This version of the process also resulted in undesirable side reactions, which were apparent from the pronounced foaming which occurred when the water was distilled off from the reaction space. The total yield of 2,6-dimethylmorpholine was 81% of theory in this case, and the product likewise contained 78% of the cis-isomer and 22% of the trans-isomer.

COMPARATIVE EXAMPLE

According to Example 8 of U.S. Pat. No. 3,083,202

450 parts by weight of 96% strength concentrated sulfuric acid were initially introduced into a stirred apparatus, and 266 parts by weight of diisopropanolamine were added at below 80° C., while stirring and cooling (2.2 moles of sulfuric acid per mole of diisopropanolamine). Thereafter, the mixture was heated at 200° C. for 3 hours, during which a total of 84 parts by weight of water (theoretical amount: 54 parts by weight) was distilled off. At the same time, vigorous evolution of sulfur dioxide was observed at 200° C., during the entire course of the reaction.

The mixture was worked up similarly to Example 6a. The product was run into 1,840 parts by weight of 20% strength sodium hydroxide solution, while stirring and cooling, and the final pH was 14. The organic phase was separated off, and distilled under reduced pressure, and the distillate was dried with 50% strength sodium hydroxide solution.

151 parts by weight (65% of theory) of 99% pure 2,6-dimethylmorpholine were obtained. The product contained 88% of the cis-isomer and 12% of the trans-isomer. (The ideal value of the total yield is 98%; cf. U.S. Pat. No. 3,088,202).

The amount of water formed under these reaction conditions is essentially above the theoretical amount; this fact together with the vigorous evolution of $SO_2$ indicate that the concentrated sulfuric acid has a substantial oxidative action in the stated temperature range.

EXAMPLE 7

The procedure was carried out similarly to Example 6a, except that the sulfuric acid and the diisopropanolamine/water mixture were fed in simultaneously at 140°–145° C. Under these reaction conditions, 2,6-dimethylmorpholine was likewise obtained in a total yield of 93% of theory. The product contained 78% of the cis-isomer.

We claim:

1. A process for the preparation of 2,6-dimethylmorpholine containing a high proportion of the cis-isomer which comprises: simultaneously metering diisopropanolamine containing from 0 to 20% of water and excess 90–120% strength sulfuric acid into the reaction zone of a reactor; stirring the reaction mixture without cooling to increase the temperature of the mixture to from 85°–170° C.; heating the reaction mixture at a temperature of from 150° to 190° C. for from 1 to 25 hours while water is distilled off; contacting the reaction mixture with a sodium hydroxide solution and distilling the resulting mixture to obtain a crude product containing 2,6-dimethylmorpholine and drying the crude product that is obtained, with sodium hydroxide, to form 2,6-dimethylmorpholine having a high proportion of the cis-monomer.

2. The process of claim 1, wherein the molar ratio of diisopropanolamine to sulfuric acid is maintained at from 1:1.0 to 1:3.0.

3. The process of claim 1, wherein the crude product is dried with concentrated sodium hydroxide solution.

4. The process of claim 3, wherein the dilute sodium hydroxide solution obtained as a result of drying the 2,6-dimethylmorpholine with concentrated sodium hydroxide solution is used to neutralize the sulfuric acid-containing reaction mixture of a subsequent batch.

* * * * *